(12) United States Patent
Rowe

(10) Patent No.: US 10,750,768 B2
(45) Date of Patent: Aug. 25, 2020

(54) PROCESS FOR MAKING A HONEY PRODUCT HAVING A LOW WATER CONTENT

(71) Applicant: IAF SCIENCE HOLDINGS LTD., Hamilton (BM)

(72) Inventor: John Lawrence Rowe, Charlottetown (CA)

(73) Assignee: IAF SCIENCE HOLDINGS LTD., Hamilton (BM)

( * ) Notice: Subject to any disclaimer, the term of this patent is extended or adjusted under 35 U.S.C. 154(b) by 0 days.

(21) Appl. No.: 14/081,659

(22) Filed: Nov. 15, 2013

(65) Prior Publication Data

US 2014/0079801 A1   Mar. 20, 2014

Related U.S. Application Data

(63) Continuation of application No. 13/144,753, filed as application No. PCT/CA2010/000058 on Jan. 15, 2010, now abandoned.

(60) Provisional application No. 61/144,824, filed on Jan. 15, 2009.

(30) Foreign Application Priority Data

Jan. 15, 2019   (CA) ..................................... 2649936

(51) Int. Cl.
| | | |
|---|---|---|
| *A23L 21/25* | (2016.01) | |
| *A61K 35/644* | (2015.01) | |
| *A23G 3/42* | (2006.01) | |
| *A23G 3/36* | (2006.01) | |

(52) U.S. Cl.
CPC ............... *A23L 21/25* (2016.08); *A23G 3/36* (2013.01); *A23G 3/42* (2013.01); *A61K 35/644* (2013.01)

(58) Field of Classification Search
CPC .......... A23L 1/08; A23L 1/0017; A23L 1/035; A61K 35/644; B65B 25/001
See application file for complete search history.

(56) References Cited

U.S. PATENT DOCUMENTS

| | | | |
|---|---|---|---|
| 2,021,450 A | 11/1935 | Hampton | .......................... 127/30 |
| 2,175,996 A | 10/1939 | Roberts | |
| 2,693,420 A * | 11/1954 | Straub | ...................... A23L 21/25 426/618 |
| 2,818,356 A * | 12/1957 | Shookhoff | ............ C13B 50/002 127/29 |
| 4,159,210 A * | 6/1979 | Chen | ........................ C13B 10/00 127/29 |
| 4,369,308 A * | 1/1983 | Trubiano | ............. A61K 9/2059 106/128.1 |
| 4,536,973 A | 8/1985 | Platt, Jr. et al. | ................. 34/182 |
| H70 H | 5/1986 | Berkowitz | |
| 4,885,035 A | 12/1989 | Slifkin | ............................ 127/58 |
| 4,919,956 A | 4/1990 | Bateson et al. | ............... 426/465 |
| 5,356,650 A | 10/1994 | Kanayama | ..................... 426/396 |
| 5,846,557 A | 12/1998 | Eisenstadt et al. | |
| 7,101,582 B2 | 9/2006 | Green | ........................... 426/494 |
| 2004/0126441 A1 * | 7/2004 | Pushpangadan | ..... A61K 36/484 424/734 |
| 2008/0057157 A1 | 3/2008 | Almeida | |
| 2009/0130199 A1 * | 5/2009 | Kovacs | .................. A61K 9/006 424/455 |

FOREIGN PATENT DOCUMENTS

| | | |
|---|---|---|
| CA | 994598 | 8/1976 |
| CA | 2430798 | 12/2011 |
| CN | 1973667 | 6/2007 |
| EP | 0431376 A1 | 6/1991 |
| EP | 0431376 B1 | 10/1993 |
| JP | 55077868 A | 6/1980 |
| JP | S55-77868 | 6/1980 |
| JP | 56-61965 | 5/1981 |
| JP | 62-186750 | 8/1987 |
| JP | 2002-207762 | 8/1990 |
| JP | 3066913 | 7/2000 |
| JP | 2003-304819 | 10/2003 |
| JP | 2016/73291 | 5/2016 |
| JP | 6179968 | 8/2017 |
| KR | 10-2005-0117807 | 12/2005 |
| WO | 98/03074 | 1/1998 |
| WO | 2008/072998 | 6/2008 |

OTHER PUBLICATIONS

RU 2005135143 May 20, 2007 1 page Derwent abstract (Year: 2007).*
Herbal Remedies. Bee Propolis Honey Lozenges. Aug. 2007 [Online] Downloaded from <URL: http://web.Archive.org/web/20070812161604/http://www.herbalremedies.com/beeprleholo1.html> 1 page.
Search Report in International Application No. PCT/CA2010/000058 dated Apr. 6, 2010.
Turkot, et al., "A Continuous Process for Dehydrating Honey." 1960 Food Technol. Wyndmoor.arserrc.gov, 4 pages.
Zamora & Chirife, *Food Control*. 17:59-64, 2006.
Cui et al., Preparation of Dry Honey by Microwave-Vacuum Drying, Journal of Food Engineering, Barking, Essex, GB, vol. 84, No. 4, Sep. 14, 2007, pp. 582-590.
Database WPI, Week 199811, Thomson Scientific, Londong, GB; AN 1998-120395 XP 002696859.
Third Party Observation filed in Canadian Patent Application No. 2,749,871 on Mar. 30, 2015.

(Continued)

*Primary Examiner* — Felicia C Turner
(74) *Attorney, Agent, or Firm* — Norton Rose Fulbright US LLP

(57) ABSTRACT

The present disclosure relates to a process for making a honey product having a low water content as well as honey products obtained using the process. The honey product retains the physical and palatable properties of untreated honey while having a prolonged shelf-life. It can be advantageously used to sweeten beverages (such as hot beverages) and in the manufacture of throat lozenges and/or confectionery.

9 Claims, No Drawings

(56) References Cited

OTHER PUBLICATIONS

TKDL Formulation ID MH6/188E1: Ziya Al-Din Abdullah Ibn Al-Baitar, *Al-Jaam'e-li-Mufradaat-al-Advia-wal-Aghzia vol. III* ($13^{th}$ *Century AD*), 1874, p. 122.
TKDL Formulation ID JA7/285W: Mohammad Azam Khan, *Muheet-e-Azam vol. II* ($19^{th}$ *Century AD*), 1887, p. 146.
TKDL Formulation ID MH3/92J: Mohammad Azam Khan, *Muheet-e-Axam, vol. I* ($19^{th}$ *Century AD*), 1896, p. 140.
TKDL Formulation ID AB/354D: Naginadasa Chaganalala Saha et al., *Bharata Bhaisajya Ratnakara vol. I*, 1999, p. 129.
Key Attributes of TKDL, MH2/06, TKDL Database, 2009, p. 4, Retrieved on Oct. 13, 2017.
Key Attributes of TKDL, MH2/140, TKDL Database, 2009, p. 92, Retrieved on Oct. 13, 2017.
Office Action issued in Indian Patent Application No. 3389/KOLNP/2011, dated Oct. 3, 2017.
Office Action with English Translation Issued in Corresponding Japanese Application No. JP 2017-019634, dated Dec. 26, 2017.

\* cited by examiner

PROCESS FOR MAKING A HONEY PRODUCT HAVING A LOW WATER CONTENT

CROSS-REFERENCE TO RELATED APPLICATIONS

This application is a continuation of U.S. application Ser. No. 13/144,753, which is a national phase application under 35 U.S.C. § 371 of International Application No. PCT/CA2010/000058 filed Jan. 15, 2010, which claims priority to U.S. Provisional Application No. 61/144,824 filed Jan. 15, 2009, and Canadian Patent Application No. 2,649,936 filed Jan. 15, 2009. The entire contents of each of the above-referenced disclosures is specifically incorporated by reference herein without disclaimer.

FIELD OF THE INVENTION

The present disclosure relates to a process for making honey product having a low water content using a specific temperatures associated with a vacuum drying step as well as honey products obtained by this process. This honey product possesses an increased shelf-life with respect to the original liquid honey. Further, its taste and color are very similar to those of the original liquid honey. In addition, the sugars in the honey product are not crystallized. The honey product can optionally be wrapped in a water-impermeable package that limits the reabsorption of water by the honey product. The honey product could be directly added to beverages to sweeten them. It can also be further processed to be used in upper respiratory care product as well as a confectionery.

BACKGROUND OF THE INVENTION

Honey is an excellent source of easily digestible sugars. It is largely composed of glucose and fructose, monosaccharides that are rapidly absorbed and metabolized by the organism. It also contains volatile components which makes it a very palatable ingredient. Honey may contain enzymes, pollen and propolis which have been recognized as having excellent health benefits.

However, the shelf-life of honey is rather limited since it will eventually (within days, weeks or months) crystallize. The crystallization of honey is not necessarily harmful, but it modifies the texture of the product to a more granulated one, which is less appealing for the consumer. In addition, during the crystallization process, water activity is increased, thereby facilitating microbial growth (such as yeast growth and/or fermentation). Further, since honey is usually packaged and stored as a liquid, it limits its application in the food industry.

Therefore, several attempts have been made to manufacture a honey product having a lower moisture content than original liquid honey. For example, unprocessed honey has been submitted to vacuum drying (refer, for example, to the abstract of JP2003304819A2, the abstract of JP02207762 as well as U.S. Pat. No. 5,356,650, U.S. Pat. No. 7,101,582), lyophilization (U.S. Pat. No. 4,885,035), extrusion drying (U.S. Pat. No. 4,919,956), thin film drying (U.S. Pat. Nos. 4,919,956, 4,536,973, 7,101,582) or even spray-drying (U.S. Pat. No. 7,101,582). However, because of the hygroscopic nature of honey, the removal of water is rather difficult and the resulting product still contains a high moisture content. For example, when untreated honey is submitted to freeze drying, it has a tendency to foam thereby limiting the amount of water that can be removed.

Because honey is supersaturated in sugars, its boiling point is much lower than a solution saturated in sugar, corn syrup or maple syrup. As such, the chemical structure changes that are induced by the exposure to heat occur more rapidly in honey than in any other sweetener or sugar-based solution. Consequently, honey has to be submitted to high temperatures for a prolonged amount of time in order to remove the water it contains. This badly affects the chemically-physical and palatable characteristics of honey. When abused by heat, the honey turns bitter and loses its typical honey flavor and physical characteristics. In order to circumvent this problem, additives have sometimes been added to the honey prior to the removal of the water.

It would be highly desirable to be provided with a honey product having a low water content as well as process for making same. The honey product would have a more prolonged shelf-life than the original liquid honey. It is preferred that the honey product possesses the distinctive taste and color of the original liquid honey.

SUMMARY OF THE INVENTION

The present disclosure relates to a honey product having a low water content. The honey product is a pure honey product.

According to a first aspect, the present disclosure provides a process for making a solid honey product having a moisture content lower than about 1% (w/w). Broadly, the process comprises (i) heating a liquid honey to a temperature of at least 98° C. to obtain a heated liquid honey; (ii) applying a pressure of at least 27 inHg to the heated liquid honey to obtain a dehydrated honey product having a moisture content lower than about 1%; and (iii) cooling the dehydrated honey to ambient temperature to obtain the solid honey product. In an embodiment, the moisture content of the solid honey product is lower than about 0.1%. In another embodiment, the process further comprises (iv) packaging the solid honey product in a water-impermeable membrane. In yet another embodiment, the process further comprises (iv) formulating the solid honey product in an upper respiratory care product (such as, for example, a throat lozenge). In still a further embodiment, the process further comprises (iv) formulating the solid honey product in a confectionery. In yet a further embodiment, the process further comprises (iv) processing the solid honey product in a granular form, a crushed form, a grounded form or a powder form. In yet another embodiment, the process further comprises (iv) adding an emulsifier, an anti-sticking agent and/or a stabilizer to the solid honey product.

According to a second aspect, the present disclosure provides a solid honey product having a moisture content having a moisture content lower than about 1% (w/w) obtained by the process described herein. In an embodiment, the honey product consisting essentially of honey and having a moisture content lower than about 1% (w/w). As used herein, the term "consisting essentially of" indicates that the honey product is composed of honey and its usual constituents (refer to the definition of honey below) and that no further additives are required to produce the honey product. In embodiment, additional elements can be added to the honey product but they should not materially affect the characteristics of the product (such as its moisture content and the absence of crystallized sugars). The present disclosure also refers to a honey product consisting of honey and having a moisture content lower than about 1% (w/w), lower than about 0.9%, lower than about 0.8%, lower than about 0.7%, lower than about 0.6%, lower than about 0.5%, lower than about 0.4%, lower than about 0.3% or lower than about 0.2%. In a further embodiment, the moisture content of the honey product is lower than about 0.1%, lower than about 0.09%, lower than about 0.08%, lower than about 0.07%, lower than about 0.06%, lower than about 0.05%, lower than about 0.04%, lower than about 0.03% or lower than about 0.02%. In still another embodiment, the moisture content of the honey product is equal to about 0.01%. According to yet another embodiment, the honey product can also contain a flavor, such as, for example, a lemon flavor (e.g. from a lemon oil). In still a further embodiment, the sugars of the honey product are in an uncrystallized form, e.g. the sugars that are contained in the honey do not crystalize. In yet a further embodiment, the honey product is solid. In still another embodiment, the honey product is wrapped in a water-impermeable package. In this particular embodiment, the honey product can have a storage time of a year (or more) without substantially reabsorbing water. According to another embodiment, the present disclosure provides a throat lozenge or an upper respiratory care and treatment product comprising the honey product described herein. According to still another embodiment, the present disclosure provides a confectionery comprising the honey product described herein. In an embodiment, the honey product has further been processed prior to the incorporation into the confectionery.

DETAILED DESCRIPTION OF VARIOUS EMBODIMENTS

In accordance with the present invention, there is provided a honey product having a moisture content of less than 1%. The honey product is not sticky or tacky and can be used as a sweetener in beverages as well as in the manufacture of a upper respiratory care and treatment product (such as a throat lozenge) or a confectionery.

The honey product described herein consists essentially of a liquid honey to which water has been removed. In an embodiment, it is pure honey to which no additive has been added. The honey product is not limited to any specific manufacturing technique. Since the honey product retains the color, characteristics and the taste of untreated honey, care must be taken in selecting an appropriate manufacturing technique that will preserve the original honey color, characteristics and taste.

According to a first aspect, the present disclosure provides a honey product consisting essentially of honey. In a further embodiment, the honey product consists of honey. As used herein, the term "honey" is referred to as a product prepared by bees from plant nectars, from plant secretions and from excretions of plant sucking insects ("honeydew"). Honey can also be referred to as the nectar and saccharine exudations of plants gathered, modified and stored by the honey bee. The chemical composition of honey varies depending on nectar source, season and production methods. Storage conditions may also influence final composition, with the proportion of disaccharides increasing over time. Fructose and glucose are present in relatively equal amounts and are the two major sugars present in honey (approximately 70% w/w). Honey also contains lesser amounts of sucrose (approximately 1%), other disaccharides and oligosaccharides. Gluconic acid, other acids and small amounts of proteins, enzymes (including glucose oxidase), amino acids and minerals may also be present. Potassium is the major mineral present. Honey is usually mildly acidic with a pH around 3.9. Moisture content is low (between 13% to 26% w/w), as is water activity (0.562-0.62).

Any liquid honey can be used in the manufacture of the honey product. The liquid honey can be raw (e.g. untreated), semi-processed (such as strained or filtered honey) or processed (e.g. pasteurized). The honey product can be made with liquid honey originating from any nectar source. Nectar sources include, but are not limited to, Acacia, Alfalfa, Apple, Blueberry, Buckwheat, Canola, Clover, Cotton, Cranberry, Dandelion, Gall berry, Goldenrod, Grape, Mesquite, Mexican, Clover, Milkweed, Palmetto, Prune, Rape, Raspberry, Sage, Sourwood, Sunflower, and/or Tupelo. The liquid honey used to manufacture the honey product can be derived from a single nectar source or from a combination of nectar sources depending on the desired properties of the final product.

The honey product defined herein has a moisture content lower than about 1% (w/w). A pure dried honey product containing more than 1% w/w of water has a tendency to become tacky. When the water content of a pure dried honey product is elevated around 2 to 3% w/w, the product is sticky to the touch. As such, because the honey product described herein has a moisture content lower than about 1% w/w, it is not tacky or sticky and can be easily be handled without substantially transferring to the surface manipulating the product (such as the skin or the package). In a further embodiment, the honey product has a moisture content lower then about 0.1% and in yet another embodiment, equal to about 0.01%.

The person skilled in the art can easily assess the percentage of moisture in a honey product using methods readily known in the art. The moisture content of a food product is usually defined through the following formula:

$$\% \text{ Moisture} = (m_w / m_{sample}) \times 100$$

where $m_w$ is the mass of the water and $m_{sample}$ is the mass of the sample. The mass of water is related to the number of water molecules ($n_w$) by the following expression:

$$M_w = n_w M_W / N_A,$$

where $M_w$ is the molecular weight of water (18.0 g per mole) and $N_A$ is Avodagro's number ($6.02 \times 10^{23}$ molecules per mole). In principle, the moisture content of a honey product can therefore be determined accurately by measuring the number or mass of water molecules present in a known mass of sample. When determining the moisture content of a food it is important to prevent any loss or gain of water. For this reason, exposure of a sample to the atmosphere, and excessive temperature fluctuations, should be minimized.

In one embodiment, a spectroscopic method can be used to determine the moisture content of the honey product. Spectroscopic methods utilize the interaction of electromagnetic radiation with materials to obtain information about their composition, e.g., X-rays, UV-visible, NMR, microwaves and IR. The spectroscopic methods developed to measure the moisture content of foods are based on the fact that water absorbs electromagnetic radiation at characteristic wavelengths that are different from the other components in the food matrix. Microwave and infrared radiation are absorbed by materials due to their ability to promote the vibration and/or rotation of molecules. The analysis is carried out at a wavelength where the water molecules absorb radiation, but none of the other components in the food matrix do. A measurement of the absorption of radiation at this wavelength can then be used to determine the moisture content: the higher the moisture content, the greater the absorption. Instruments based on this principle are commercially available and can be used to determine the moisture content in a few minutes or less.

In another embodiment, a chemical reaction, such as a colometric reaction, can be used for the determination of moisture in the honey product. The Karl Fischer titration is often used for determining the moisture content of foods that have low water contents (e.g. dried fruits and vegetables, confectionery, coffee, oils and fats). It is based on the following reaction:

$$2H_2O+SO_2+I_2 \rightarrow H_2SO_4+2HI$$

This reaction was originally used because HI is colorless, whereas $I_2$ is a dark reddish brown color, hence there is a measurable change in color when water reacts with the added chemical reagents. Sulfur dioxide and iodine are gaseous and would normally be lost from solution. For this reason, the above reaction has been modified by adding solvents (e.g., $C_5H_5N$) that keep the $S_2O$ and $I_2$ in solution, although the basic principles of the method are the same. The food to be analyzed is usually placed in a beaker containing solvent and is then titrated with Karl Fischer reagent (a solution that contains iodine). While any water remains in the sample the iodine reacts with it and the solution remains colorless (HI), but once all the water has been used up any additional iodine is observed as a dark red brown color ($I_2$). The volume of iodine solution required to titrate the water is measured and can be related to the moisture content using a pre-prepared calibration curve. The precision of the technique can be improved by using electrical methods to follow the end-point of the reaction, rather than observing a color change.

One particular advantage of the product described herein is that, during its production, no additives are being added to facilitate water removal or to limit the adhesion of the product to its packaging membrane. However, in an embodiment, it is contemplated that a flavor is added to the honey product described after it has been evaporated. The added flavor may be, for example, a sweet or a savory flavor. Sweet flavors include, but are not limited to fruits (peach, pear, apple), citrus (orange, lemon, lime), berry (raspberry, strawberry, blueberry), spice (vanilla, cinnamon, clove, lavender), caramel, butterscotch, maple. Savory flavors include, but are not limited to, ginger, pepper (black, white, pink, green, hot), etc. Other flavors, such as coffee, tea, herbal tea and/or alcohol, can also be added. In an embodiment, the flavor can be derived from an oil. If a flavor is added to the honey product, care must be taken that the added flavor does not substantially augments the moisture content of the final honey product higher than about 1% w/w.

Another advantage of the honey product described herein is that the majority of the sugars present are in an uncrystallized form. As used herein the term "uncrystallized" refer to the absence of sugar crystals that can be felt in the mouth and/or visible to the naked eye. The honey product has a smooth texture and does not contain granulated honey crystals which can be seen by the naked eye or felt in the mouth.

During storage, liquid honey has a tendency to take on a semi-solid state known as "crystallized" or "granulated honey". This natural phenomenon happens when the glucose present in honey spontaneously precipitates out of the supersaturated honey solution. By becoming a glucose monohydrate, glucose loses water and takes the form of a crystal. As used herein, a "crystal" or a "honey crystal" is referred to as a solid body with a precise and orderly structure that can be felt in the mouth or be visible to the human eye. Once formed, the honey crystals organize into a lattice which immobilizes other components of honey in a suspension thus creating the semi-solid state. The water that was previously associated with the glucose becomes available for other purposes, thus increasing the moisture content in some parts of the container of honey. Because of the increased moisture, the liquid honey becomes more susceptible to microbial growth (such as yeast growth).

In still a further embodiment, the honey product is a solid honey product. It is contemplated that the honey product will be solid at ambient temperature and at normal atmospheric pressure. As used herein "solid honey product" refers to a substance derived from honey that is not liquid and that can be used as a source of nourishment. The honey product can be easily handled because it is not tacky or soft.

In yet another embodiment, the honey product is a pure and/or dried honey product. As used herein, the term "pure" honey product refers to a product that is free or substantially free from exogenous additives with respect to the original liquid honey. On the other hand, a "dried" honey product refers to the fact that the moisture content is limited to no more than 1% w/w.

Because of the hygroscopic nature of honey, the honey product will tend to reabsorb water if it is not placed in a water impermeable package. For example, if the product is left at ambient temperature, within a couple of days, it will tend to become tacky and, within a couple of weeks, it will tend to become sticky or soft. As such, in order to prolong the shelf life of the product, it has to be packaged in a water-impermeable membrane. As used herein, a "water-impermeable package" or "water-impermeable membrane" refers to a material that limits the transmission of water vapor. In an embodiment, the water vapor transmission rate (WVTR) of the "water-impermeable" package or membrane is below 0.1 gm/100 $in^2$ or below about 0.01 gm/100 $in^2$. Because the honey product is mainly used as a food or as a food additive, the package must be of food or pharmaceutical grade. Further, since the package can optionally be submitted to heat to seal it around the honey product, the package or membrane must also be resistant to heat.

When the honey product is wrapped in a water-impermeable package, its storage time is of about a year or even more (depending on the WVTR of the package). During storage, the product does not substantially reabsorb water and as such its water content is substantially constant. As used herein, a honey product that does not "substantially" reabsorb water is a honey product that possesses a water content of less than about 1% w/w during its storage. As indicated above, when the water content of the honey product exceeds 1% w/w, the honey product becomes tacky.

Additional uses of the honey product are also contemplated. Once produced, the honey product can be further processed for use in other food applications such as confectionary, dessert topping, sweet ingredient. The solid honey product can be further powdered, crushed, ground and/or granulated for these additional applications.

Particles can thus be made from the solid honey product and used in various food applications. For example, when a coarser particle is required, the solid honey can be processed into a "granular" form particles having a size distribution that ranges between about 0.25 and 2 mm. On the other hand, when a finer particle is needed, the solid honey product can be processed into a "powder" form particles having a size distribution that ranges between 62.5 to 125 m. The size distribution of the particles can be assessed by the techniques known in the art, such as the Gates-Gaudin- Schuhmann method, the Rosin-Rammler method, the modified Gaudin-Meloy method, the Log-normal method and/or the modified beta method.

When particles of the solid honey product are produced, it may be desirable to add a further agent to the particles to prevent or delay water absorption. Such further agent can be an emulsifier, an anti-sticking agent and/or a stabilizer, including, but not limited to bee wax, carnauba wax, maltodextrin, dextrose or other food processing aids.

Similar to what has been indicated above, the particles of the solid honey can also be packaged in a water-impermeable membrane to slow down, delay or prevent water reabsorption.

The honey product as described herein can be advantageously used to sweeten a beverage. When the honey product is placed in an aqueous-based beverage, it reabsorbs water and dissolves to sweeten the beverage. The application of the honey product is not limited to a specific type of beverage or to beverages having a specific temperature. However, the sweetening process will be accelerated in hot beverages. Hence, in an embodiment, the honey product is advantageously used in hot beverages such as coffee, tea and herbal tea.

Since honey has been recognized as an antimicrobial product, the honey product described herein can be used in the manufacture of upper respiratory care and treatment products such as throat lozenges. The upper respiratory care and treatment product can either consist of the honey product described herein or can be combined with other additives used in the art for their manufacture.

Because of the excellent palatable properties of honey, the honey product described herein can be further processed into a confectionery. In order to introduce the honey product into a confectionery, and as indicated above, it can be physically processed (crushed, powdered, coated in a solution) and/or flavors can be added. Alternatively or concomitantly, the manufacturing process of the product can also be altered to introduce additional components of the confectionery.

As indicated above, the honey product is not limited to a specific manufacturing technique. In one advantageous embodiment and as shown below, the liquid honey is submitted to vacuum drying to lower its water content and generate the honey product. The time, temperature and pressure variables used should be designed to generate a honey product having similar characteristics (smell and taste) as the original liquid honey. However, upon water evaporation, it is assumed that the honey will have a decrease in flavor intensity and stickiness and that the sweetness level of product could be perceived as different than in the liquid honey.

In an embodiment, the liquid honey is first heated from ambient temperature to at least 98° C. under a pressure of at least 27 inHg. As it is known in the art, the time to reach the desired temperature will depend on the amount of liquid honey that is being processed as well as the content of original the liquid honey (such as its moisture content). Once the temperature of the liquid honey reaches at least 98° C., the temperature is not further raised but the vacuum (e.g. pressure of at least 27 inHg) is maintained until the desired moisture is reached (less than about 1% w/w). As it is known in the art, the time required to reach the desired moisture content also depends on the amount of honey that is being processed and the content of the original liquid honey (such as its moisture content). Optionally, the honey product can be dispensed and packaged.

The present invention will be more readily understood by referring to the following examples which are given to illustrate the invention rather than to limit its scope.

EXAMPLE I

Production of Honey Product

The following ingredients were used in the production of the honey product:
Liquid honey containing a blend of white clover, red clover and/or dandelion that is extracted, liquefied, filtered and short time pasteurized; and
Optionally, lemon oil.

The following material was also used in the production of the honey product:
Water-impermeable food-grade packaging;
Food grade PVC packaging trays; and
High barrier to moisture food grade sealing film.

The following equipment was used in the production of the honey product:
Weighing scale;
Electronic universal mixer;
Thermocouple Thermometer;
Infra-red (IR) moisture meter; and
Heat sealer.

Lab and pilot plant trials were carried out to determine the evaporation, dispensing and packaging processes of the honey product. In addition, the lemon flavored honey product was developed following the sourcing of an appropriate lemon flavoring.

Untreated honey was first submitted to a gross evaporation step where liquid honey was gradually heated from ambient temperature to at least 98° C. and at least at 27 inHg vacuum. Once at 98° C., the temperature of the honey was held, and the pressure was applied (at least at 27 inHg vacuum) until the desired moisture content of the product was reached (less than about 1% w/w as measured by the IR moisture meter). Through this process, an evaporation could take place while maintaining the light brown appearance and flavor of natural untreated honey. The evaporated honey was then individually dispensed. The product was cooled and solidified at ambient temperature. The honey product was packaged and heat sealed. The honey product was further packaged into cardboard boxes and stored prior to its characterization. Optionally, a lemon flavoring was added to the evaporated honey prior to the dispensing of the honey product. The honey product possessed a shelf life of one year.

EXAMPLE II

Honey Product Characterization

Prior to dispensing the evaporated honey product in the molding trays, a 5 g. aliquot was removed to determine the moisture content using and IR moisture meter (as described in Example I) in order to rapidly assess the moisture content. The moisture content of the honey product was evaluated between 0.0 to 1.1% (w/w).

A single batch of the honey product was further characterized. Table 1 shows the various analyses performed and the method used.

TABLE 1

Analyses performed on the honey product.

| Analysis | Method Reference |
|---|---|
| Total Metals Analysis in Food by inductively coupled plasma atomic emission spectrometry (ICP-AES) | EPA 6010 |
| Ash | AOAC 923.03 |
| Beta-Carotene | AOAC 922.04, 922.06 |
| Calories | Calculation |
| Carbohydrates | Calculation |
| Cholesterol | AOAC 976.26/994.1 |
| Fatty Acid Profile by GC/FID | AOAC 996.06 |
| KJ | Calculation |
| Moisture (Karl Fischer) | AOAC 926.08 925.10 |
| Protein | AOAC 992.15 |
| Retinol | AOAC 992.04 992.06 |
| Sugar Profile | AOAC 980.13 |
| Total Dietary Fibre | AOAC 991.43 |
| Vitamin A IU/100 g | AOAC 992.04, 992.06 |
| Vitamin A RE/100 g | AOAC 992.04, 992.06 |
| Vitamin C (Ascorbic Acid) | CFIA/QFCL-001-01 mod |

The results of these analyses are shown in Table 2.

TABLE 2

Results obtained from the analyses listed in Table 1.

| Analysis | Units | Results |
|---|---|---|
| Energy | Cal/100 g | 386 |
|  | kJ/100 g | 1615 |
| Protein | g/100 g | 0.21 |
| Fat: GC | g/100 g | 0.073 |
| Polyunsaturates | g/100 g | 0.004 |
| Monounsaturates | g/100 g | 0.023 |
| Saturates | g/100 g | 0.041 |
| Trans | g/100 g | 0.001 |
| Omega-3 Polyunsaturated Fatty Acids | g/100 g | 0.001 |
| Omega-6 Polyunsaturated Fatty Acids | g/100 g | 0.003 |
| Cholesterol | mg/100 g | <1.0 |
| Carbohydrates | g/100 g | 96.1 |
| Total Sugars | g/100 g | 80.9 |
| Fructose | g/100 g | 44.8 |
| Glucose | g/100 g | 35.4 |
| Sucrose | g/100 g | ND |
| Maltose | g/100 g | 0.7 |
| Lactose | g/100 g | ND |
| Total Dietary Fibre | g/100 g | <0.1 |
| Sodium | mg/100 g | ND |
| Potassium | mg/100 g | 80 |
| Vitamin A | IU/100 g | ND |
|  | RE/100 g | ND |
| Retinol | ug/100 g | ND |
| Beta Carotene | ug/100 g | <10 |
| Vitamin C | mg/100 g | 1.1 |
| Calcium | mg/100 g | 11 |
| Iron | mg/100 g | ND |
| Moisture: Karl Fischer | g/100 g | 0.349 |
| Ash | g/100 g | 0.1 |

Per serving of 20 g., the honey product contains 80 calories, 15 mg. of potassium and 19 g. of carbohydrate (16 g. of sugar).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A process for making a solid honey product consisting of honey and optionally a flavor and/or an upper respiratory care ingredient, wherein the solid honey product has a moisture content lower than 0.1% (w/w), said process comprising:
heating a liquid honey to a temperature of 98° C. to obtain a heated liquid honey;
applying a pressure of 27 inHg to the heated liquid honey to obtain a dehydrated honey product having a moisture content lower than 0.1%; and
cooling the dehydrated honey product to obtain the solid honey product.

2. The process of claim 1, further comprising packaging the solid honey product in a water-impermeable membrane.

3. The process of claim 1, further comprising formulating the solid honey product in an upper respiratory care product.

4. The process of claim 3, wherein the upper respiratory care product is a throat lozenge.

5. The process of claim 1, further comprising formulating the solid honey product in a confectionery.

6. The process of claim 1, further comprising processing the solid honey product in a granular form, a crushed form, a grounded form or a powder form.

7. The process of claim 1, wherein the solid honey product is capable of remaining a solid for at least one year of storage.

8. The process of claim 2, wherein the solid honey product is capable of remaining a solid for at least one year of storage.

9. The process of claim 3, comprising adding the flavor or the upper respiratory care ingredient to the liquid honey or to the dehydrated honey product.

* * * * *